(12) United States Patent
Knas et al.

(10) Patent No.: US 10,943,680 B1
(45) Date of Patent: Mar. 9, 2021

(54) INTELLIGENT HEALTH-BASED BLOCKCHAIN

(71) Applicant: MASSACHUSETTS MUTUAL LIFE INSURANCE COMPANY, Springfield, MA (US)

(72) Inventors: Michal Knas, Monson, MA (US); Jiby John, Suffield, CT (US); Richard Ferry, Springfield, MA (US); Krzysztof Gibadlo, Springfield, MA (US)

(73) Assignee: Massachusetts Mutual Life Insurance Company, Springfield, MA (US)

( * ) Notice: Subject to any disclaimer, the term of this patent is extended or adjusted under 35 U.S.C. 154(b) by 343 days.

(21) Appl. No.: 16/125,175

(22) Filed: Sep. 7, 2018

Related U.S. Application Data

(60) Provisional application No. 62/555,243, filed on Sep. 7, 2017.

(51) Int. Cl.
| | |
|---|---|
| *G16H 10/60* | (2018.01) |
| *H04L 9/08* | (2006.01) |
| *G06F 21/31* | (2013.01) |
| *H04L 9/06* | (2006.01) |
| *G06F 16/27* | (2019.01) |
| *G06F 16/182* | (2019.01) |
| *G06F 16/18* | (2019.01) |

(52) U.S. Cl.
CPC .......... *G16H 10/60* (2018.01); *G06F 16/182* (2019.01); *G06F 16/1805* (2019.01); *G06F 16/27* (2019.01); *G06F 21/31* (2013.01); *H04L 9/0643* (2013.01); *H04L 9/0819* (2013.01); *H04L 9/0861* (2013.01); *H04L 2209/38* (2013.01)

(58) Field of Classification Search
CPC ..... G16H 10/60; G06F 16/1805; G06F 16/27; G06F 16/182; G06F 21/31; H04L 2209/38; H04L 9/0861; H04L 9/0819; H04L 9/0643
See application file for complete search history.

(56) References Cited

U.S. PATENT DOCUMENTS

| | | | | |
|---|---|---|---|---|
| 9,526,420 | B2 * | 12/2016 | Fish | A61B 5/749 |
| 9,608,829 | B2 * | 3/2017 | Spanos | H04L 9/3242 |
| 9,734,304 | B2 * | 8/2017 | Blackadar | G16H 40/67 |
| 9,849,364 | B2 * | 12/2017 | Tran | G06K 9/00342 |

(Continued)

OTHER PUBLICATIONS

McKnight et. al, "Commodifying Trust Trusted Commerce Policy Intersecting Blockchain and IoT", Aug. 12, 2017.*
Antonopoulous, "Mastering Bitcoin", O'Reilly Media, Dec. 2014.*

*Primary Examiner* — Steven S Kim
(74) *Attorney, Agent, or Firm* — Foley & Lardner LLP

(57) ABSTRACT

A computer implemented method for safe, efficient, and fraud-proof continuous retrieval of health data is disclosed. The method comprises receiving a request to update a record associated with a user blockchain comprising identification information associated with a health tracker, a health tracker server, and user authentication data; generating an instruction to receive user data based on the identification information and user authentication data; receiving health data from the health tracker server; retrieving and verifying the validity of the user's latest blockchain; storing the data in a volatile memory; and creating a new block instance corresponding to the data.

20 Claims, 7 Drawing Sheets

(56) References Cited

U.S. PATENT DOCUMENTS

| | | | |
|---|---|---|---|
| 9,870,508 B1* | 1/2018 | Hodgson | G11B 27/10 |
| 2016/0027029 A1* | 1/2016 | Poole | G06Q 30/0205 |
| | | | 705/7.34 |
| 2016/0120716 A1* | 5/2016 | Ribble | A61B 5/4818 |
| | | | 5/616 |
| 2017/0177898 A1* | 6/2017 | Dillenberger | H04L 9/3236 |
| 2017/0228371 A1* | 8/2017 | Seger, II | G06F 16/2379 |
| 2018/0075028 A1* | 3/2018 | Ruschin | G06Q 10/00 |
| 2018/0225660 A1* | 8/2018 | Chapman | G06Q 20/3827 |
| 2018/0227119 A1* | 8/2018 | Bibera | H04L 63/083 |
| 2018/0255090 A1* | 9/2018 | Kozloski | H04L 67/02 |
| 2018/0278691 A1* | 9/2018 | Vergara, Jr. | A61B 5/1118 |
| 2019/0026364 A1* | 1/2019 | Sankovsky | A61B 5/7267 |
| 2019/0189254 A1* | 6/2019 | Roennow | A61B 5/6813 |

* cited by examiner

|  | Sleep pattern | Steps | Heart rate | Blood pressure | Driving time |
|---|---|---|---|---|---|
| 702 — Wearable Device 1 | N/A | 1200 | 80 | 120 | N/A |
| 704 — Wearable Device 2 | N/A | N/A | 82 | N/A | N/A |
| 706 — IoT Device 1 | 8 hours | N/A | N/A | N/A | N/A |
| 708 — IoT Device 2 | N/A | N/A | N/A | N/A | 3 hours |

|  | Sleep pattern | Steps | Heart rate | Blood pressure | Driving time |
|---|---|---|---|---|---|
| 710 — JSON File | 8 hours | 1200 | 81 | 120 | 3 hours |

FIG. 7

INTELLIGENT HEALTH-BASED BLOCKCHAIN

CROSS-REFERENCE TO RELATED APPLICATIONS

This application claims priority to U.S. Provisional Patent Application Ser. No. 62/555,243, filed Sep. 7, 2017, which is hereby incorporated by reference in its entirety.

TECHNICAL FIELD

This application relates generally to minimizing data manipulation risk by efficiently generating blockchains.

BACKGROUND

As the blockchain technology has improved, many institutions generate blockchains to store users' sensitive information. For example, many institutions create health blockchains where users' health data (e.g., data received from various health-tracking devices) is stored onto a blockchain and used for health-related purposes. Even though blockchains offer a secure method of data storage, generating and maintaining a blockchain requires heavy calculations processing power. For instance, when storing a user's health related data onto a blockchain, a server must collect the data periodically, generate a block instance, communicate with different network nodes within the blockchain, identify a latest valid blockchain, and update the blockchain, which is a computer-intensive process that requires heavy computing power. This process is especially burdensome when each health-tracking device transmits multiple batches of data per day.

In order to overcome the above-mentioned problem, some conventional and existing methods have implemented a software solution where data is received less frequently. For example, a central server may instruct a health-tracking device to transmit collected data in batches. As a result, instead of receiving health-related data multiple times a day, the central server receives health-related data once every few weeks, which reduces how frequently the server must update the blockchain. Even though this solution possibly solves the heavy computing power needed to generate, update, and maintain the blockchain, it increases the chance of fraudulent activity before the user's data is stored onto the blockchain because cyber attackers are allotted more time to compromise the data before it is transferred and stored onto the user's blockchain. Therefore, conventional and existing solutions may alleviate one problem but create other technical problems.

SUMMARY

For the aforementioned reasons, there is a need for a more accurate system and method that would allow users to accurately upload, store, and access health records, profile, and other pertinent health information in a more efficient and fraud-proof manner than possible with human-intervention or conventional solutions. Disclosed herein are systems and methods for dynamic generation of an intelligent health-based blockchain.

In an embodiment, a computer-implemented method comprising: receiving, by a first server from an electronic device operated by a user, a request to update a blockchain of the user, the request comprising identification information associated with a health-tracking sensor, a second server associated with the health-tracking sensor, and user authentication data; generating, by the first server, a first instruction to receive health data captured by the health-tracking sensor, the first instruction comprising the identification information associated with the health-tracking sensor and the user authentication data; upon transmitting the first instruction to the second server, receiving, by the first server, health data captured by the health-tracking sensor; storing, by the first server, health data in a volatile memory storage; periodically updating, by the first server, the blockchain of the user based on the health data stored in the volatile memory storage where updating comprises: retrieving, by the first server, a plurality of latest valid block instances associated with the user from a plurality of network nodes, each block instance comprising encrypted health data associated with the user and a corresponding hash value, wherein each block instance is stored in a database associated with at least one of the plurality of network nodes; comparing, by the first server, the hash value associated with each block instance within the plurality of latest valid blockchains with each respective hash value associated with each respective block instance within each latest valid blockchain received from each network node of the plurality of network nodes; upon a number of matching hash values satisfying a pre-determined threshold: generating, by the first server, a new block instance comprising the health data stored within the volatile memory storage and a new hash value based at least on one of the user, the health data captured by the health-tracking sensor, the second server, and the user computing device, according to a hashing algorithm.

In another embodiment, a computer system comprising an electronic device operated by a user; a health-tracking sensor configured to captured health data associated with the user, the health-tracking device further configured to transmit the captured health data to a first server; a plurality of network nodes where each network node is configured to store at least one block instance of a blockchain of a user; a second server in communication with the health-tracking sensor, the first server, the plurality of network nodes, and the electronic device, the second server configured to receive, from the electronic device, a request to update the blockchain of the user, the request comprising identification information associated with the health-tracking sensor, a second server associated with the health-tracking sensor, and user authentication data; generate a first instruction to receive health data captured by the health-tracking sensor, the first instruction comprising the identification information associated with the health-tracking sensor and the user authentication data; upon transmitting the first instruction to the first server, receive health data captured by the health-tracking sensor; store health data in a volatile memory storage; periodically update the blockchain of the user based on the health data stored in the volatile memory storage where updating comprises: retrieve a plurality of latest valid block instances associated with the user from the plurality of network nodes, each block instance comprising encrypted health data associated with the user and a corresponding hash value, wherein each block instance is stored in a database associated with at least one of the plurality of network nodes; compare the hash value associated with each block instance within the plurality of latest valid block instances with each respective hash value associated with each respective block instance within each latest valid blockchain received from each network node of the plurality of network nodes; upon a number of matching hash values satisfying a pre-determined threshold: generate a new block instance comprising the health data stored within the volatile memory storage and a new hash value based at least on one of the user, the health data captured by the health-tracking sensor, the second server, and the user computing device, according to a hashing algorithm.

It is to be understood that both the foregoing general description and the following detailed description are explanatory and are intended to provide further explanation of the various embodiments disclosed herein.

BRIEF DESCRIPTION OF THE DRAWINGS

The accompanying drawings constitute a part of this specification and further illustrate an embodiment of the present disclosure and together with the specification, explain various embodiments of the present disclosure.

FIG. 7 illustrates an example of aggregating data from different devices into a uniform JSON file, according to an embodiment.

DETAILED DESCRIPTION

Figure 1:
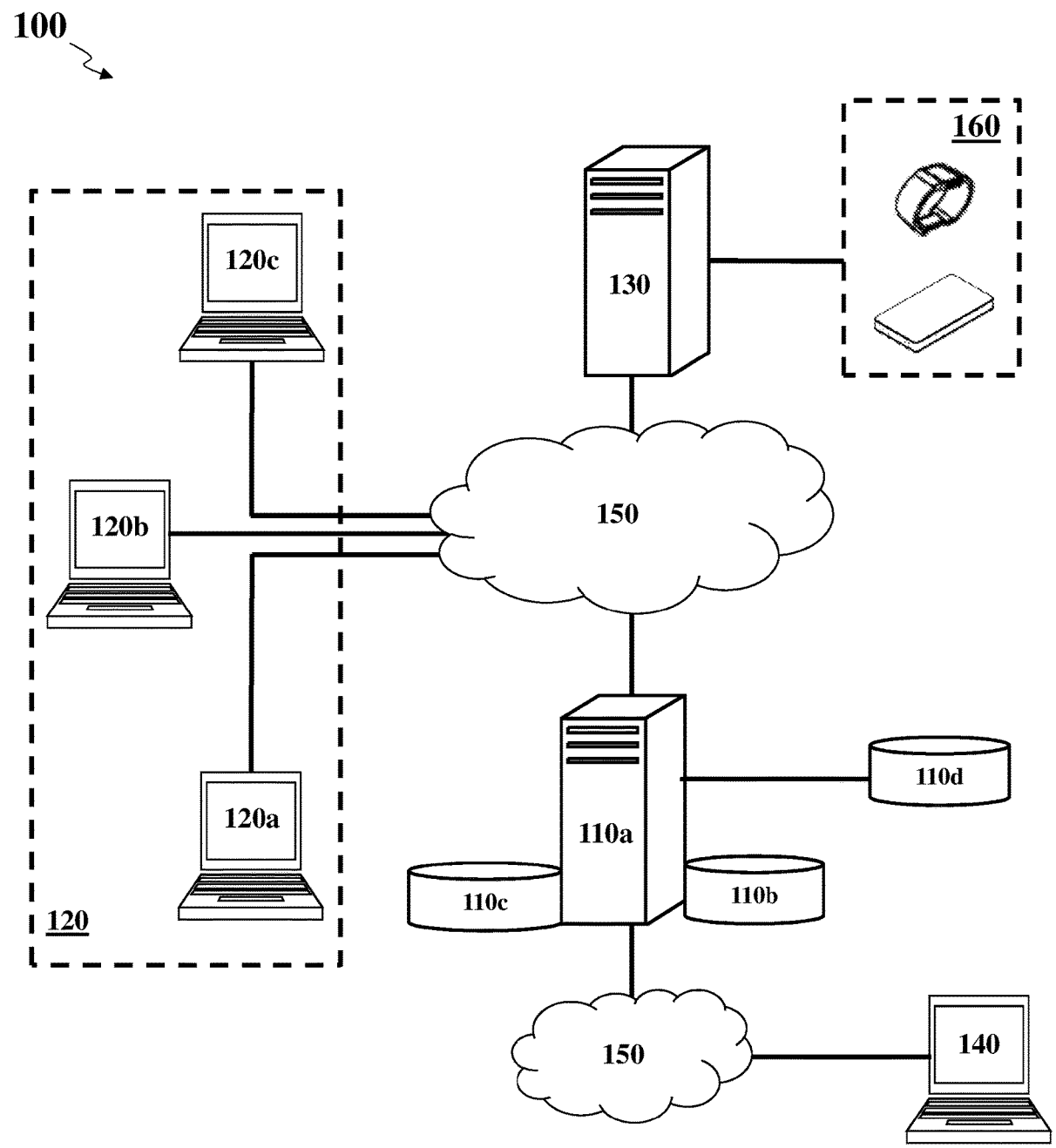
FIG. 1 illustrates an example of a computer system for generating an intelligent health-based blockchain, according to an embodiment.

Reference will now be made to the exemplary embodiments illustrated in the drawings, and specific language will be used here to describe the same. It will nevertheless be understood that no limitation of the scope of the embodiments is thereby intended. Alterations and further modifications of the inventive features illustrated here, and additional applications of the principles of the embodiments as illustrated here, which would occur to a person skilled in the relevant art and having possession of this disclosure, are to be considered within the scope of the present disclosure.

FIG. 1 illustrates components of a system 100 for generating an intelligent health-based blockchain, according to an exemplary embodiment. The system 100 may comprise an analytics server 110a, system database 110b, a key storage database 110c, volatile data storage 110d, a client device 140, third party database 130, and distributed network nodes 120a-c. Aspects of the system 100 may be configured to employ and manage a system blockchain, sometimes referred to in the art as a "distributed ledger," and may include blockchain-based distributed ledger software (e.g., Hyperledger, Ethereum, Openchain, and TerraLedger). The system blockchain may operate as a distributed database that stores data records associated with users' health and transaction documents, where the data records stored on the system blockchain may be blocks of data (e.g., block instances) that are hosted (e.g., locally stored) on distributed network nodes 120a-c or different databases associated with said nodes.

The data stored in records within system databases 110b may vary from the data stored in blocks of the system blockchain hosted on network nodes 120a-c. Furthermore, each block may not be accessible to other network nodes, however the analytics server 110a may access all block instances. The analytics server 110a may also store one or more block instances in the system database 110b. In some embodiments, the analytics server 110a may generate a duplicate of one or more block instances within a health blockchain and store said block instances in the system database 110b. While the analytics server 110a may dictate accessibility and transmit instructions to other parties within system 100, each network node within the distributed network nodes 120a-c (e.g., creator of the block instance) or the client (via the client device 140) may prevent others within system 100 from accessing at least portions of the data within one or more block instances. For example, while generating a block instance, the analytics server may 110a designate a portion of the data within the block instance as private.

An analytics server 110a may generate and display a user interface on the client device 140, each node within the distributed network nodes 120a-c. An example of the user interface generated and hosted by the analytics server 110a may be a website. The analytics server 110a may host a website accessible to end-users, where the content presented via the various webpages may be controlled based upon each particular user's role. The analytics server 110a may be any computing device comprising a processor and non-transitory machine-readable storage capable of executing the various tasks and processes described herein. Non-limiting examples of such computing devices may include workstation computers, laptop computers, server computers, laptop computers, and the like. While the system 100 includes a single analytics server 110a, some embodiments the analytics server 110a may include any number of computing devices operating in a distributed computing environment.

The analytics server 110a may execute software applications configured to display the user interface (e.g., host a website), which may generate and serve various webpages to client device 140 or each network node within the distributed network nodes 120a-c. The website may be used to generate and access data stored on a system database 110b or a blockchain hosted by nodes 120a-c and managed by the analytics server 110a. In some implementations, the analytics server 110a may be configured to require user authentication based upon a set of user authorization credentials (e.g., username, password, biometrics, cryptographic certificate).

In such implementations, the analytics server 110a may access a system database 110b configured to store user credentials, which the analytics server 110a may be configured to reference in order to determine whether a set of entered credentials (purportedly authenticating the user) match an appropriate set of credentials that identify and authenticate the user. Similarly, in some implementations, the analytics server 110a may generate and serve webpages to a client device 140 based upon a user's role within the system 100 (e.g., administrator, employee, or the health service provider). In such implementations, the user's role may be defined by data fields and input fields in user records stored in the system database 110b. The analytics server 110a may conduct the authentication of the user and user's role by executing an access directory protocol (e.g. LDAP). The analytics server 110a may then generate webpage content, access or generate data stored in the system database 110b, and access or generate data stored in the blockchain instances, according to the user's role defined by the user record in the system database 110*b*.

The analytics server 110*a* may also generate, access, and update blockchain instances hosted on system nodes 120*a-c*, according to instructions received from a client device 140, or any of the nodes within the system nodes 120*a-c*. Software executed by the analytics server 110*a* may provide blockchain services to users interacting with the analytics server 110*a*. For example, the analytics server 110*a* may render blockchain services to the client device 140, or nodes 120*a-c* via the user interface provided to these computing devices. In some embodiments, the analytics server 110*a* may update and query records in the system database 110*b* according to the instructions received from the client device 140.

The analytics server 110*a* may then generate block instances for the system blockchain, where the block instances contain data from the records of the system database 110*b*. The application server may then update a local instance of the system database 110*b*, and subsequently instruct network nodes 120*a-c* to update the instances of the system blockchain stored locally on each of the network nodes 120*a-c*. The analytics server 110*a* may generate each new block instance with a timestamp or other data that links the new block instance with existing block instances on the blockchain. As an example, when the analytics server 110*a* generates a new user record in the system database 110*b*, the analytics server 110*a* then generates a hash value for the user based upon one or more data fields of the user record. The analytics server 110*a* then generates a new block instance for the system blockchain within the local instance of the blockchain stored in the analytics server 110*a* (or a database associated with the analytics server 110*a*). The analytics server 110*a* then transmits the updated block instance to each respective network node 120*a-c*. The network nodes 120*a-c*, in turn, may update the local instances of the blockchain stored on each of the network nodes 120*a-c*.

In some configurations, the analytics server 110*a* may store data received from the health-tracking devices and/or the third-party database 130 on to the volatile data storage 110*d*. For instance, upon receiving data from a user's health-tracking device (e.g., health-tracking devices 160) the analytics server 110*a* may store the received data onto the volatile data storage 110*d* instead of a traditional database or instead of generating a block instance for the data received.

The volatile data storage 110*d* may be a static random access memory structure that retains data bits in its memory as long as power is being supplied. Unlike dynamic RAM, which stores bits in cells consisting of a capacitor and/or a transistor, the volatile data storage 110*d* may utilize a memory storage system that does not have to be periodically refreshed. The volatile data storage 110*d* provides faster access to data. In a non-limiting example of the memory structure utilized by the volatile data storage 110*d* may be a cache memory system. Cache memory is a high-speed static random access memory that allows a computer microprocessor to access the content stored more quickly than regular random access memory.

As described below, the analytics server 110*a* may create a blockchain based on data stored on to the volatile data storage 110*d*, instead of creating a block instance for the data received. This process improves quality of the blockchain (e.g., because all block instances correspond to a uniform interval) and requires less computing power. Furthermore, the analytics server 110*d* may also purge the volatile memory 110*d* periodically or after creating and/or updating the users' blockchain. In this way, the analytics server 110*a* ensures that users' data is stored on to their respective blockchains, which decreases the chances of data compromise.

Additionally or alternatively, the analytics server 110*a* may also perform various data analytics using the health data collected. For instance, the analytics server 110*a* may execute one or more scoring protocols, using a user's health data, to identify an overall score for each user.

In operation, when a user instructs the analytics server 110*a* to conduct a service requiring a query of the block instances of the blockchain or when a user (or a network node) requires modification/update of a block instance, the analytics server 110*a* may conduct a poll of all the parties associated with the blockchain (e.g., the network nodes 120*a-c* and/or the client device 140) to identify the queried or modified data, based on the hash values identifying the block instances, and then determine whether the data within the identified block instances is accurate. The analytics server 110*a* may then await a response from a predetermined quorum of network nodes 120*a-c*, or the client device 140 to confirm the data in the blocks. The analytics server 110*a* may then proceed with a rendering the service or modifying the block using the data blocks of the blockchain, if a predetermined threshold number of network nodes 120*a-c* indicates that the blocks at issue match the blocks of the instance stored locally on each of the network nodes 120*a-c* or approve the modification.

In some configurations, a pre-determined number of quorums may always not be necessary to proceed. For example, when the analytics server receives an instruction from the client device 140 to update a blockchain associated with a previous health service provider (stored in node 120*b*), the analytics server may await receipt of approval from 120*b* even if a quorum is met.

The analytics server 110*a* may generate block addresses for data to be retrieved from blockchain instances of the system blockchain. Machine-readable computer files containing various forms of documents (e.g., PDF, DOC, and XLS) may be uploaded and stored into the system database 110*b*. The analytics server 110*a* may also generate a hash value of the document, where the application uses the hash value or other identifier values to reference the file from the system database 110*b*. The analytics server 110*a* may then generate the block address for the file by generating a hash of the document and a hash value of the immediately preceding block data or block address. This block address may then be stored into the system database 110*b* in a document record along with the file and any number of additional data field entries related to the computer file.

In operation, the analytics server 110*a* or network nodes 120*a-c* may reference the block of the blockchain containing the file according to the block address. The analytics server 110*a* may generate additional blocks and corresponding block addresses on the system blockchain in a similar manner (e.g., generating a hash value for a block containing user data and then generating a new block address using the block address of the preceding block). Block addresses may be generated in any number of combinations of hashed block data and/or hashed block addresses from the new block and one or more preceding blocks, such that the address of the new block is dependent upon, or otherwise linked to, at least the immediately preceding block.

In some implementations, a system blockchain may contain data regarding a client's health. The analytics server 110*a* may manage a health blockchain, where each block instance within the blockchain represents a health service provider or another institution relevant to the client's health (e.g., educational institution or the like) and store pertinent data within the system database 110b. Non-limiting examples of what may be stored in the system database 110b may include: user records that may comprise data fields describing users (e.g., user data), such as user credentials (e.g., username, passwords, biometrics, encryption certificates), block addresses for blocks on the system blockchain, user account data, user roles or user permissions; document records that may comprise machine-readable computer files (e.g., word processing files), health records inputted by each previous health service provider, parsed portions of such computer files, or metadata associated with computer files; and application data that may include software instructions executed by an analytics server 110a or data used by the such applications executed by the analytics server 110a.

User records stored on the system database 110b may comprise a data field containing a user-identifying hash value generated by the analytics server 110a according to a hashing algorithm implemented by a system blockchain, when a new user record is generated or updated. The hash value may be generated using one or more data fields that describe the user, which may be entered by a user via a website portal or pulled from the user record in the system database 110b. The hash value may be a unique identifier for the particular user record, and may be used by various computing devices of the system 100 to reference the user data, which may be stored in the system database 110b and/or on blocks of the system blockchain that is hosted on network nodes 120a-c. The system database 110b may be hosted on any number computing devices comprising a non-transitory machine-readable storage medium and capable of performing the various tasks described herein. As shown in FIG. 1, the system database 110b may be accessed by the analytics server 110a via one or more networks.

Document records stored on the system database 110b may comprise a data field containing document-identifying hash values generated by the analytics server 110a according to a hashing algorithm implemented by a system blockchain, when a new document record containing a machine-readable computer file (e.g., PDF, DOC, XSL), such as an health recognition or award documents, is generated or updated. The hash value may be generated using one or more data fields that describe the computer file, which may be uploaded by a user via a website portal or pulled from the document record within the system database 110b. The hash value may be a unique identifier for the particular document record, and may be used by various computing devices of the system 100, such as the system database 110b, to reference the computer file or metadata describing the computer file, which may be stored in the system database 110b and/or on block instance of the system blockchain that is hosted on network nodes 120a-c.

A key storage database 110c, sometimes referred in the art as a high security module, key appliance, certificate authority, or the like, may be a computing device configured to manage and distribute encryption keys and cryptographic certificates to various computing devices in the system 100 according to predetermined roles and rules. In some implementations, encryption keys may be used for authentication of users when users log into a website (or any other user interface provided to the users) hosted on the analytics server 110a. In some implementations, encryption keys may be used to encrypt the data within the block instance of the system blockchain. Additionally or alternatively, encryption keys may be used to confirm, or "sign," data transfers to confirm to a data transfer recipient that the data originated from a known party. The key storage database 110c may be hosted on any number computing devices comprising a non-transitory machine-readable storage medium and capable of performing the various tasks described herein. As shown in FIG. 1, the key storage database 110c may be accessed by the analytics server 110a via one or more networks, but the key storage database 110c may also be accessed by the client device 140 and network nodes 120a-c to retrieve or confirm encryption keys or encryption key signatures. Moreover, the key storage database 110c may be hosted on the same physical computing device functioning as the analytics server 110a and/or an analytics server 110a.

Network nodes 120a-c may represent an institution relevant to the user's health history (e.g., a health service provider and the like) and may host one or more blocks of the system blockchain. A network node 120a-c may be any computing device comprising a processor and a non-transitory machine-readable storage medium capable of performing the various tasks and processes described herein. Non-limiting examples of a network node may be a workstation computer, laptop computer, tablet computer, and server computer. Although the network nodes 120a-c are described as storing blocks of the blockchain in FIG. 1, other computing devices, such as an analytics server 110a, may host blocks of the blockchain. Each network node 120a-c locally stores an instance of the system blockchain in the storage medium of the system blockchain, and further executes a software application that instructs the network node 120a-c on generating and querying blocks within the locally stored blockchain instance.

In operation, a network node may generate new blocks on a locally stored instance of the system blockchain according to data received from an analytics server 110a or other network nodes 120a-c. In some instances, the analytics server 110a may update a local block instance stored on the analytics server 110a (e.g., within the system database 110b), and then instructs one or more of the network nodes 120a-c to update each block instance stored in their local storage (e.g., local database). Moreover, the analytics server 110a may query the block instances of the system blockchain according to a block address stored in the system database 110b. When the analytics server 110a executes the query of the blocks on the system blockchain, the analytics server 110a may poll the network nodes 120a-c to determine the most recent data on the system blockchain (e.g., latest valid blockchain). The analytics server 110a may be confident that the data at block is the desired data according to a voting mechanism encoded within the blockchain software executed by the network nodes 120a-c. Each network node 120a-c may receive the query for the block instance and block address, and return a response to the analytics server 110a indicating whether the block address contains the desired data. The analytics server 110a may select this method to combat possible fraud and to be certain that data in the blockchain is resistant to corruption, as each block instance on each network node 120a-c would need to be corrupted in the same way so that each block address is corrupted in the same way. Similarly, in this way, the analytics server 110a may be prevented from acting on obsolete data. For instance, a network node 120a-c may attempt to modify information about a user's health history. By modifying the information within the block instance, the hash value of said block instance may change, which would result in the block instance being disconnected from other block instances within the blockchain.

A client device 140 may be any computing device allowing a user to interact with analytics server 110a via analytics server 110a. The client device 140 may execute an Internet browser or local application that access the analytics server 110*a* in order to issue requests or instructions to the analytics server 110*a* to access the system blockchain (e.g., transmit instructions to the analytics server 110*a*). The client device 140 may transmit credentials from user inputs to the analytics server 110*a*, from which the analytics server 110*a* may authenticate the user and/or determine a user role. The client device 140 may comprise any number of input devices configured to receive any number of data inputs, including various types of data inputs allowing for authentication (e.g., username, passwords, certificates, and biometrics). The client device 140 may be any computing device comprising a processor and non-transitory machine-readable storage medium allowing the client device 140 to perform the various tasks and processes described herein. In some embodiments, the analytics server 110*a* may also automatically receive more information (e.g., updates) from a third-party server such as the third party database 130 or a server associated with said database.

As an example of the client device 140 operation, the client device 140 may execute an Internet browser that accesses the analytics server 110*a* hosting a health history website (or any other user interface) that allows the user to access and/or manage his/her health history and resume). The client devices 140 of the investor-user or a promoter-user may be used upload machine-readable computer files (e.g., PDF, DOC, XSL) containing health information. The computer files may be stored into document records in a system database 110*b*, which may then be added to block instances of the system blockchain, where the block instances are accessible according to block addresses that are then stored into the document record for the particular computer file. The client device 140 may issue queries or instructions to the analytics server 110*a* via the webpages generated by the analytics server 110*a*, which then instruct the analytics server 110*a* to query the block instances on the network nodes 120*a*-*c*, and, in some instances, perform various tasks, such as retrieving or updating a file from the system database 110*b*.

System 100 may also include the third-party server 130, which may be a server associated with the health-tracking devices 160. In one or more embodiments, health-tracking devices 160 may be any computing device (e.g., sensor) that is configured to measure the user's health-related data. For instance, health-tracking devices 160 may be configured to measure biometric, movement, exercise data, number of flights of stairs climbed, heart rate, amount of time standing, or other data associated with a user, such as various wearable or fitness-tracking devices.

Health-tracking devices 160 may also refer to certain Internet of things (IoT) devices configured to capture and transmit users health-related data comprising a processor, memory, power resources to perform various tasks, and network connectivity that enables the electronic device to connect and exchange data with other electronic devices. For example, the health-tracking devices 160 may refer to any physical devices, home appliances, and other items embedded with electronics, software, sensors, and network connectivity. In the home network, IoT devices may be smart devices of lighting, heating (such as smart thermostats), ventilation, air conditioning (HVAC), and security, as well as home appliances such as washer/dryers, ovens or refrigerators/freezers. Furthermore, IoT devices may be smart devices providing intelligent personal assistant services, such as Amazon Echo®, Google Home®, and the like. Such IoT devices may collect data on a user's behavior, habit, lifestyle, and other health attributes. For example, the data from a smart mattress may include information on the consumer's sleep pattern. The data from the telematics in a car may include information on the consumer's driving behavior. The data from Amazon Echo® and Google Home® may include information on the consumer's life routines that may be related to user's health (e.g., grocery shopping list).

In some configurations, health-tracking devices 160 may periodically transmit health-related data to the third-party server 130. As described below, the analytics server 110*a* may retrieve health-related data captured by the health-tracking devices 160 and create/update a user's blockchain.

Figure 2:
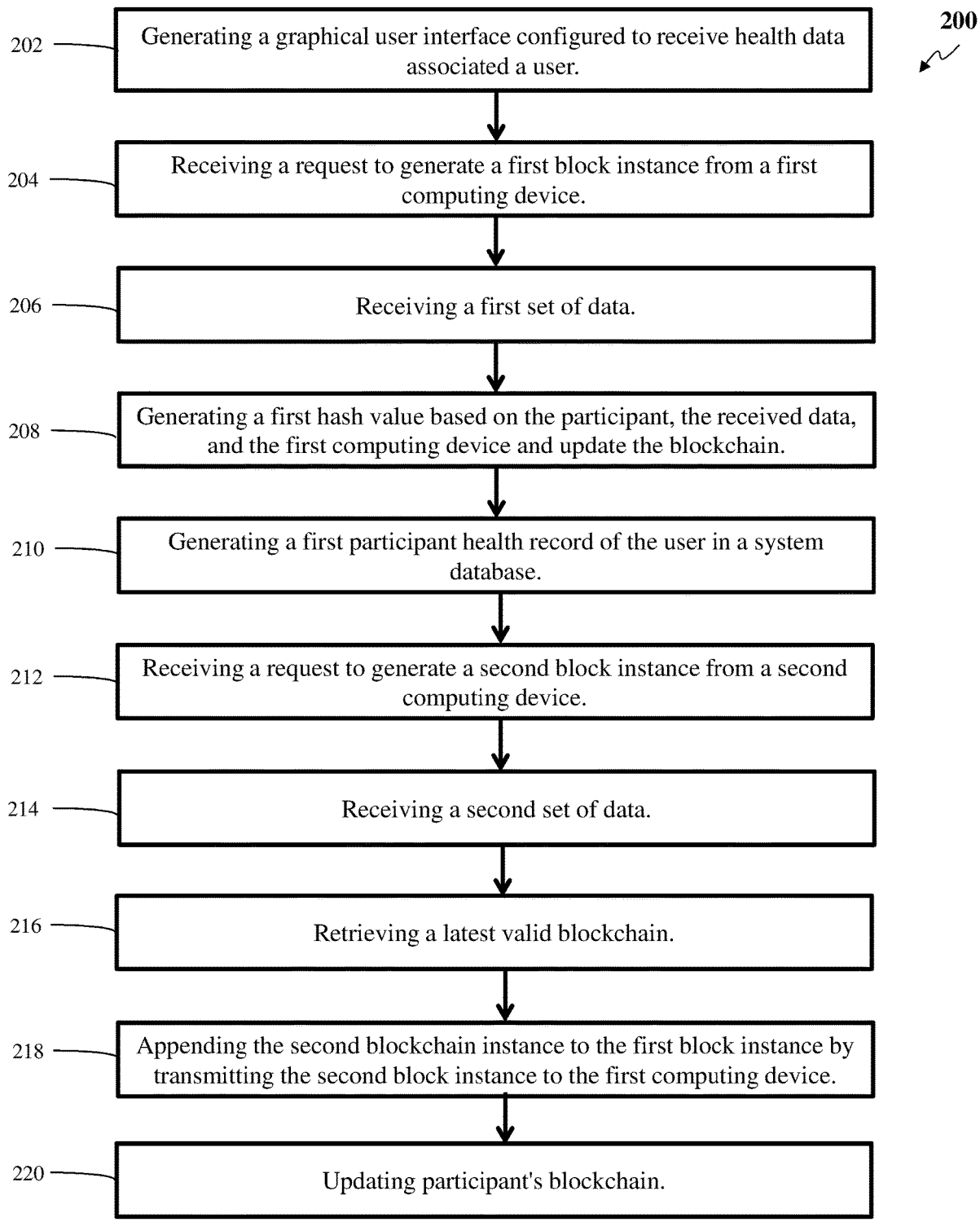
FIG. 2 illustrates a flowchart depicting operational steps for generating an intelligent health-based blockchain, according to an embodiment.

FIG. 2 illustrates execution of an exemplary method 200 for generating an intelligent and secure electronic health blockchain, according to an exemplary embodiment. Other embodiments may comprise additional or alternative steps, or may omit some steps altogether.

At step 202, the analytics server may generate a graphical user interface comprising a plurality of input fields configured to receive health data associated a user. The analytics server may generate a graphical user interface in order to provide health record services to variety of clients (e.g., health service providers, users, insurance companies, and the like). In an embodiment, the graphical user interface may be a website hosted by the analytics server, which is available to different clients. The purpose of said website may be to collect health information, provide a platform to securely upload health data, link health-related devices, and/or possibly retrieve health data from the website. The graphical user interface may act as an intermediary between different parties involved within a user's overall well-being and may be a central and "one stop" place for adding, updating, and/or retrieving health data. While the graphical user interface is described herein as a central management tool, neither the analytics server nor the graphical user interface deviates from the spirit of the distributed nature of the blockchain technology. The analytics server provides a management tool to reduce computational burden of keeping records of data stored within various and sometimes-unrelated databases. As explained above, block instances may be stored in individual client databases (network nodes).

At step 204, the analytics server may receive a first request to generate a health record associated with a user from a first computing device, wherein the blockchain is associated with health of the user. The analytics server may receive a request for a secure blockchain-based health record associated with the user. In some embodiments, an administrator associated with a computing device (e.g., a health service provider computing device) may log into a website hosted by the analytics server to generate or update the user's health record.

At step 206, the analytics server may receive a first set of health data associated with the user. The administrator associated with the first computing device (e.g., a first network node) may use the GUI provided by the analytics server to input data regarding the user. In an embodiment, the data received by the analytics server may be identification of the user, education, salary, benefits, health insurance, medical history, and the like. The analytics server may also receive computer readable files related to the user's health. For example, the administrator operating the first computing device may upload a computer readable file (e.g., PDF, DOC, DOCX, XLS, and the like) related to the user's health, such as a PDF file of previous diagnosis and/or medication prescriptions.

The data received from the first computing device (e.g., the data to be added to the first block instance) may be a command a computer function itself. For example, the data within the first block instance may comprise an instruction executable by the analytics server, the first computing device, or any other computing device or electronic source to perform a set of tasks. For example, company A may (instead of uploading each health document individually) transmit an authentication token. Once the token is activated, it permits an internal search within the database of company A. Utilizing this functionality, company A has effectively given authorization and access to the analytics server to search for all related documents within a database internal to company A. In an embodiment, the user may authorize the analytics server to search within a health-related entity associated with the user. For example, the user may grant the analytics server access to his health-related device or an insurance company and the analytics server may query all the necessary data.

The analytics server may automatically receive the first set of data from an electronic source with little or no human intervention. The analytics server may utilize an application programming interface (API) to receive the user's health data. For example, an API locally installed on the first computing device, in direct communication with the analytics server, may query all relevant data (e.g., data associated with the user) and transmit the data to the analytics server. Additionally or alternatively, the analytics server may periodically (e.g., in accordance to a predetermined time period or based on received threshold from the first computing data or another electronic source) instruct the API to transmit user's health data back to the analytics server. In other embodiments, the analytics server may generate and transmit an instruction to a database associated with the first computing device configured to query and receive the user's health data. For example, a health service provider may not need to update the information and request a new block instance every time a user's health record is updated. Upon discovering a change of health record status, the analytics server may notify the first computing device to update the user's information and/or automatically generate an instruction configured to receive the user's health data.

Upon receiving the first set of data from the first computing device (or other sources associated with the first computing device), the analytics server may instruct a blockchain service application executed by the analytics server to create a block instance. In some embodiments, the first computing device may use a blockchain service application, which may not be executed by the analytics server. For example, the first computing device (or any other network node associated with the blockchain) may use a third party blockchain service application. In those embodiments, the analytics server may still have access to the blockchain and may still generate the hash values as described below. The first set of data (e.g., user's health data from the first computing device) may be stored onto a block instance and stored locally on a database associated with the first computing device, according to instructions of the blockchain service application and/or the analytics server. In some embodiments, the analytics server may duplicate and locally store a copy of the block instance within the system database.

At step 208, the analytics server may generate a first hash value based at least on one of the user, the received first set of data, and/or the first computing device, according to a hashing algorithm. The analytics server may also update the first block instance with the first hash value, wherein the block instance is stored within the first computing device (or in a database associated with the first computing device).

The analytics server may generate a hash value based on the network node (e.g., the first computing device), the user (e.g., user's identification or other identifying values associated with the user), and/or the data received form the node (e.g., the first set of data). The hash value may be non-interactive and/or may have no secret/encryption keys that have to be managed by a central server or any other relying party (e.g., the analytics server or another central server). The hash value may be a cryptographic hash function. For example, in some embodiments, the hash value may be a string of alphanumerical values. The analytics server may generate the hash value based on the received data from the first computing device. For example, data inputted in the one or more data fields of the graphical user interface may be hashed according to a predetermined hashing algorithm, combined together, and then stored onto the block instance. The analytics server may use this method to combat possible fraud because making the slightest change to the data within the blockchain may result in modification of the hash value, therefore an unauthorized modification of the data within a block instance may result in the block instance being disconnected from the blockchain by disconnecting the hash value of the subsequent blockchain instances. The analytics server may transmit the hash value to the first computing device and update the first block instance with the first hash value.

In some embodiments, the analytics server may hash portions of the first block separately to create intermediate hash values and generate a final hash value based on the intermediate hash values and store the final hash value in the first block instance. Alternatively and/or additionally, the analytics server may hash the entire content of the first block instance to generate the final hash value and store the hash value in the first block instance. Furthermore, the analytics server may store the hash value in an internal database to be verified or retrieved later.

At step 210, the analytics server may generate a user health record of the user in a system database configured to store a plurality of user health records, the user health record comprising one or more data fields containing the first set of data. The analytics server may store data associated with the first block instance within the system database (as described in FIG. 1). For example, the analytics server may record the hash value and/or the first set of data associated with the user within the system database. For example, the analytics server may keep a record of which network node has access to or has stored which block instance. The analytics server may use the stored data to access the network node and retrieve data within one or more block instances stores within the network node (or a database associated with the network node). In some embodiments, the analytics server may use the hash value in order to identify the block instance and/or the network.

At step 212, the analytics server may receive a second request to update the health record by generating a second block instance for a second computing device. The analytics server, similar to step 202, may receive a request to update user's health blockchain (e.g., generate another block instance and append to the user's health blockchain). In an embodiment, a second administrator utilizing a second computing device may log in the website hosted or otherwise associated with the analytics server and request to add information regarding the user's health. The second computing device (e.g., second network node) may be associated with a second health service provider or health-related entity (e.g., laboratory administrator updating the user's health blockchain with the latest blood work results).

At step 214, the analytics server may receive a second set of health data associated with the user from the second computing device. As explained above, the analytics server may, similar to step 204, receive the user's health data from the second computing device (e.g., second node). In an embodiment, the data received by the analytics server may include identification of the user, education, employee salary, benefits, start date, and the like. As described above, the data received from the second computing device (e.g., the data to be added to the second block instance) may be a command a computer function itself. For example, the data within the second block instance may comprise an instruction executable by the analytics server, the second computing device, or any other computing device or electronic source to perform a set of tasks. The analytics server may also receive computer readable files related to the user's health. For example, the administrator operating the first computing device may upload a computer readable file (e.g., PDF, DOC, DOCX, XLS, and the like) related to the user's health, such as a PDF file of an health award or XLS file of the user's billable hours. In some embodiments, the analytics server may utilize an API to receive the user's health data. For example, an API locally installed on the first computing device and in direct communication with the analytics server may query all relevant data (e.g., data associated with the user) and transmit the data to the analytics server.

As explained above, the analytics server may also automatically receive the first set of data from an electronic source with little or no human intervention. The analytics server may utilize an API to receive the user's health data. For example, an API locally installed on the second computing device and in direct communication with the analytics server may query all relevant data (e.g., data associated with the user) and transmit the data to the analytics server. The analytics server may periodically (e.g., in accordance to a predetermined period of time or based on received threshold from the second computing data) instruct the API to transmit user's health data. In other embodiments, the analytics server may generate and transmit an instruction to a database associated with the second computing device configured to query and receive the user's health data. For example, a health service provider may not need to update the information and request a new block instance every time a user is given a health-related service. Upon discovering a change in the user's health status, the analytics server may notify the second computing device and automatically generate a new blockchain instance.

At step 216, the analytics server may retrieve the latest valid blockchain, wherein the valid blockchain is confirmed by the first computing device. The analytics server may also generate a second hash value identifying the user, the second set of data, and the second computing device, according to a hashing algorithm. In some implementations, to deploy the second block instance to the user's health blockchain, the analytics server may poll the network nodes associated with the blockchain instances within the user's health blockchain and determine the latest valid blockchain. The analytics server may use a predetermined threshold for determining the latest valid blockchain. For example, the analytics server may query the network nodes (e.g., the first computing device) for the latest blockchain instance. If the analytics server receives the same blockchain from 51% of the network nodes, the analytics server may determine that the received blockchain is the latest valid blockchain. In some embodiments, the analytics server may generate and transmit an instruction to all the network nodes associated with other block instances within the health blockchain and notify the parties that a validation process has been initiated and that the network node's participation is requested. The predetermined threshold is set upon the level of integrity required for the data and instructions stored in the analytics server or the blockchain. In some embodiments, the analytics server may receive the level of integrity (e.g., the threshold to determine the latest valid blockchain) from the client device (e.g., the user), the first computing device, the second computing device, or any other network node or computing device associated with the blockchain. The analytics server may use a higher predetermined threshold for data requiring a higher level of security and integrity, for example, recognition point transfers or sensitive recommendation/data transfer. While the present embodiment only describes two computing device for the simplicity purposes, the user's health blockchain may include several computer nodes and the analytics server may poll all the nodes associated with a blockchain to receive the latest valid blockchain. In an embodiment, the analytics server may contact every node associated with the blockchain and request to receive each node's latest valid blockchain. Upon receipt of the latest valid blockchain of each network node (including the hash values for each block instance) the analytics server may match the received hash values from each node with each other. Upon the number of positive matches satisfying a threshold, the analytics server assumes that the received blockchain is the latest valid blockchain.

At step 218, the analytics server may append the second block instance to the first block instance by transmitting the second block instance to the first computing device. The application server may append the second block instance to the latest valid blockchain. The analytics server may also generate second hash value using the user's identification, data received from the second computing device (e.g., second network node), and/or the identification of the second node. The analytics server may generate the second hash value based on the network node (e.g., the second computing device), the user (e.g., user's identification or other identifying values associated with the user), and/or the data received form the node (e.g., the second set of data). The second hash value may be non-interactive and/or may have no secret/encryption keys that have to be managed by a central server or relying party (e.g., the analytics server or another central server).

The second hash value may be a cryptographic hash function. For example, in some embodiments, the second hash value may be a string of alphanumerical values. The analytics server may generate the second hash value based on the received data from the second computing device. For example, data inputted in the one or more data fields of the graphical user interface may be hashed according to a predetermined hashing algorithm, combined together, and then stored to the blockchain instance. As explained above, the analytics server may hash portions of the first block separately to create intermediate hash values and generate a final hash value based on the intermediate hash values and store the final hash value in the first blockchain instance.

Additionally or alternatively, the application server may hash the entire content of the first block instance to generate the final hash value and store the hash value in the first blockchain instance. The second hash value may also be, wholly or partially, based the first hash value. In some embodiments, the analytics server may generate the second hash value using the first hash value (e.g., associated with the first computing device and generated in step 208). In those embodiments, the second hash value associated with the second block instance may include or be based on the first hash value. The analytics server may append the second block instance to the first block instance (of the latest valid blockchain) by transmitting the second hash value and a block address associated with the second block instance to the first computing device. Simply put, the analytics server may transmit the latest block instance to all the nodes associated with the blockchain. The hash values, which are interrelated, ensure the connectivity of the second block instance to the preceding block instance of the latest valid blockchain (e.g., the first block instance).

At step 220, the analytics server may update the second block instance with the second hash value, wherein the second block instances stored within the second computing device. In some instances, the analytics server may generate instructions (utilizing the blockchain services hosted by the analytics server) and update all the nodes associated with the hash value associated with the second blockchain instance. The analytics server may update the user's health blockchain by transmitting the newly generated block instance to all the network nodes associated with the health blockchain. For example, the analytics server may transmit the second block instance to the first node and the first block instance to the second node. By transmitting the block instances, the analytics server ensures that all the network nodes possess the latest valid block instance or block addresses associated with the latest valid block instances within the blockchain.

In some configurations, the analytics server may generate private and/or public keys for various computing devices described above to access user's blockchain. In order to create these keys, the analytics server may use asymmetrical encryption methods such as private and public key encryption methods.

The analytics server may, upon performing the requested action, store the unique private key and/or a timestamp indicating the administrator, the requested actions, and the time performed into the block instance. This information may be public and visible to other network nodes. For example, another network node may be able to examine each public block instance and determine the administrator who generated said block instance or modified/updated it. In some embodiments, the analytics server may be configured to communicate with other distributed ledger/blockchain managers (not shown) in a network of blockchains to provide for consensus or other safeguards that ensure that data being added to or otherwise being altered in the distributed ledger is allowable. The analytics server may provide (e.g., display on the GUI) the key for the user to share with others. For example, a user may share his health-related data with a third party or a potential employer.

Figure 3:
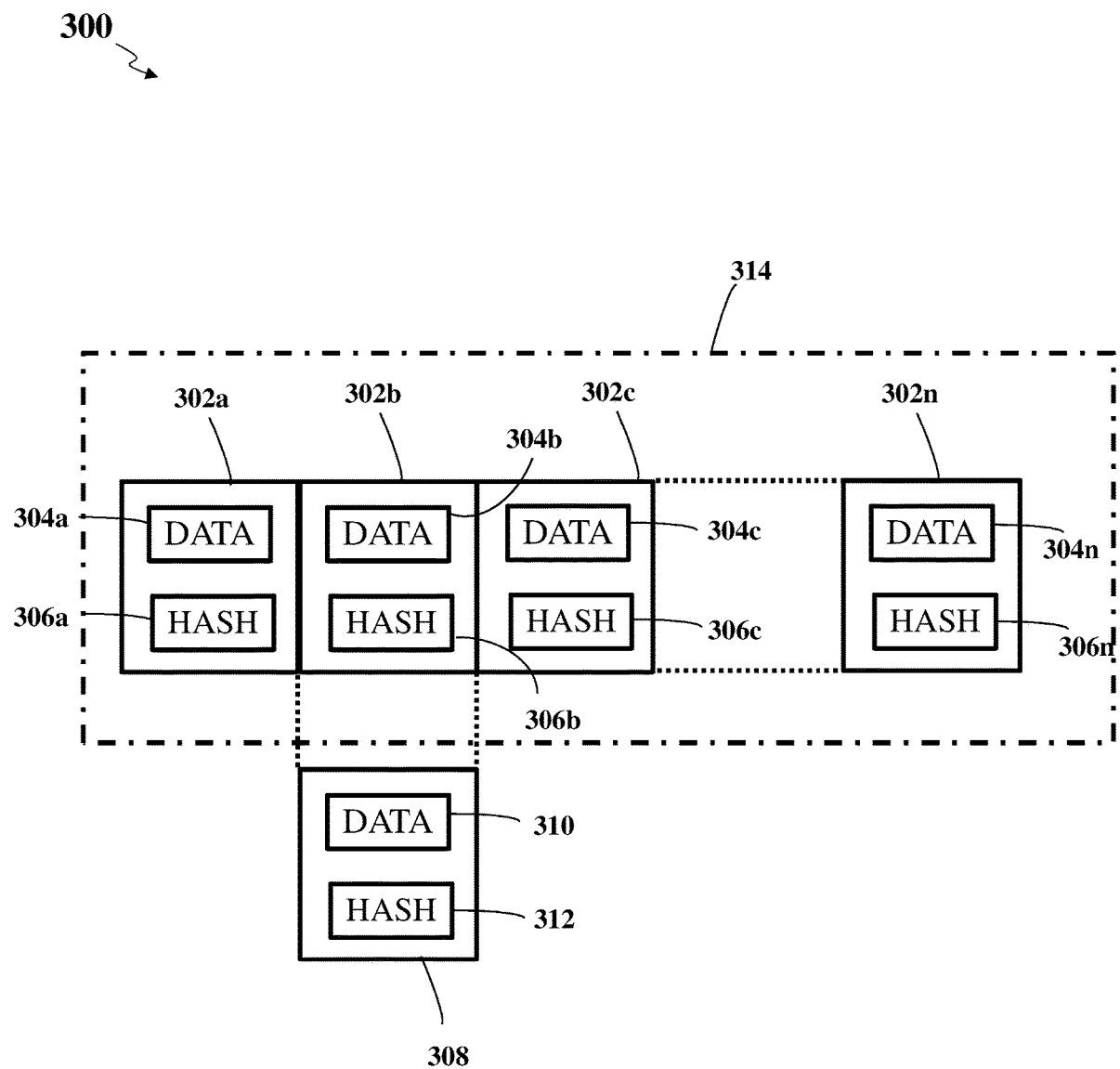
FIG. 3 graphically illustrates an example of appending multiple block instances, according to an embodiment.

Referring now to FIG. 3, an example of a user's health blockchain comprising different block instances is illustrated. As depicted in FIG. 3, a blockchain 314 comprises block instances 302a-302n (collectively 302) may include data 304a-304n (collectively 304) that enables information, such as health data, machine-readable code/documents, and other metadata associated with a user. Also contained in the blockchain instances are hash values 306a-306n (collectively 306) that are used to link each of the block instances to the preceding blockchain instances or blockchain formed by the preceding blockchain instances, as understood in the art.

As explained above, the analytics server may generate (or instruct a blockchain service to generate) the block instance 302a. The analytics server may receive data 304a from the first computing device (e.g., first node) via GUI provided by the analytics server on the first computing device/network node (steps 202-206 of FIG. 2). For example, an administrator using the first computing device may log in a website hosted or otherwise associated/managed by the analytics server and transmit data 304a to the analytics server. Upon generation of block instance 302a, the analytics server may generate hash value 306a based on the data 304a, the first node (e.g., the first computing device), identifier information (e.g., time stamp and/or geolocation), and/or an identification of the user (e.g., step 208 of FIG. 2). The analytics server may also generate (or instruct a blockchain service to generate) the block instance 302b.

The analytics server may receive data 304b from a second computing device (e.g., second network node) via GUI provided by the analytics server on the first computing device (steps 212-214 of FIG. 2). For example, an administrator using the second computing device may log in a website hosted or otherwise managed by the analytics server and transmit data 304b to the analytics server. The analytics server may also generate hash value 306b based on the data 304b, the second network node (e.g., identifier information such as time stamp, geolocation, and/or a computing device identifier), and/or a reference to the system database associated with the analytics server. The hash value 306b may also include information regarding the hash value 306a. The analytics server may incorporate the hash value 306a into the hash value 306b in order to append the block instance 302b to the block instance 302a (step 218 of FIG. 2). The analytics server may subsequently poll all the nodes in order to ensure the highest integrity of the blockchain by appending the latest block instance to the latest valid blockchain instances. Using this method blockchain instances within the blockchain 314 may be appended to the preceding blockchain instance. The analytics server may generate blockchain instance 302c-n using the same methods explained above in order to continuously update blockchain 314. As depicted, block instances 302a, 302b, 302c, and 302n are connected because of synchronization of hash values 306a, 306b, 306c, and 306n.

In some configurations, additional information, such as an identifier associated with network nodes adding or updating the data could also be included within the blockchain or incorporated within the hash value. As an example, if a network node modifies or adds any data to the blockchain, an identifier associated with the computing device who contributed to creating or modifying the data may be included in the respective block. In some embodiments, the identifier may include a time stamp (e.g., data regarding the time of data modification or creation) and/or a geolocation (e.g., data regarding the location within which the data modification or creation has occurred). The identifier may also be incorporated within the hash value and may be used by the analytics server as a part of the hashing algorithm. Such identification information may be used as a veracity scale factor that the information is true and accurate. The analytics server may also transmit the blockchain instances to all the network nodes within the blockchain in order to preserve the integrity of the blockchain. For example, the analytics server may transmit the hash value 306c (e.g., the hash value generated for block instance 302c based on data 304c received from a third node) to the first node (e.g., the first computing device storing the block instance 302a) and the second node (e.g., the second computing device storing the block instance 302b).

Modification of data within a block instance may disconnect that block instance from the blockchain. The analytics server may use this method to combat possible fraud or unauthorized modification of the data within blockchain instances. For example, if the second administrator using the second computing device modifies data 304*b* within block instance 302*b*, the hash value 306*b* will also be modified. As explained above the hash value 306*b* may be based on (or at least partially based on) data 304*b*; therefore if data 304*b* is modified to data 310, hash value 306*b* will also be modified to hash value 312. Modification of hash value 306*b* to hash value 312 may break the link between block instance 302*b* and block instance 302*c*. The analytics server may generate a new block instance 308 including the modified data 310 and a newly generated hash value 312. However, the analytics server may not attempt to append or include the newly generated block instance 308 within the blockchain 314. The analytics server may append block instance 308 to block instance 302*b* by linking hash value 312 to hash value 306*b* (e.g., generating the hash value based (at least partially) on hash value 306*b*. In operation, the analytics server may encounter such modification when a health service provider desires to update or insert additional material the user's health blockchain. For example, a second network node (e.g., the network node owner of block instance 302*b*) may be a previous health service provider to the user. The second network node may desire to update certain information (e.g., result of a drug treatment) to the user's health blockchain. Since the analytics server protects the integrity of the health blockchain, the analytics server may not allow the second network node to modify data 304*b*. The analytics server may provide the second network node the option to generate a new block instance (e.g., the block instance 308) and append to the second network node's previous block instance (block instance 302*b*). The analytics server may also transmit the block instance 308 to all the network nodes within blockchain 314; therefore, while all the network nodes within the blockchain 314 are aware of the block instance 308, they are also aware that block instance 308 contains updated and modified data. In some embodiments, the analytics server may poll all the existing network nodes within the health blockchain before appending the block instance 308 to block instance 302*b*.

Figure 4:
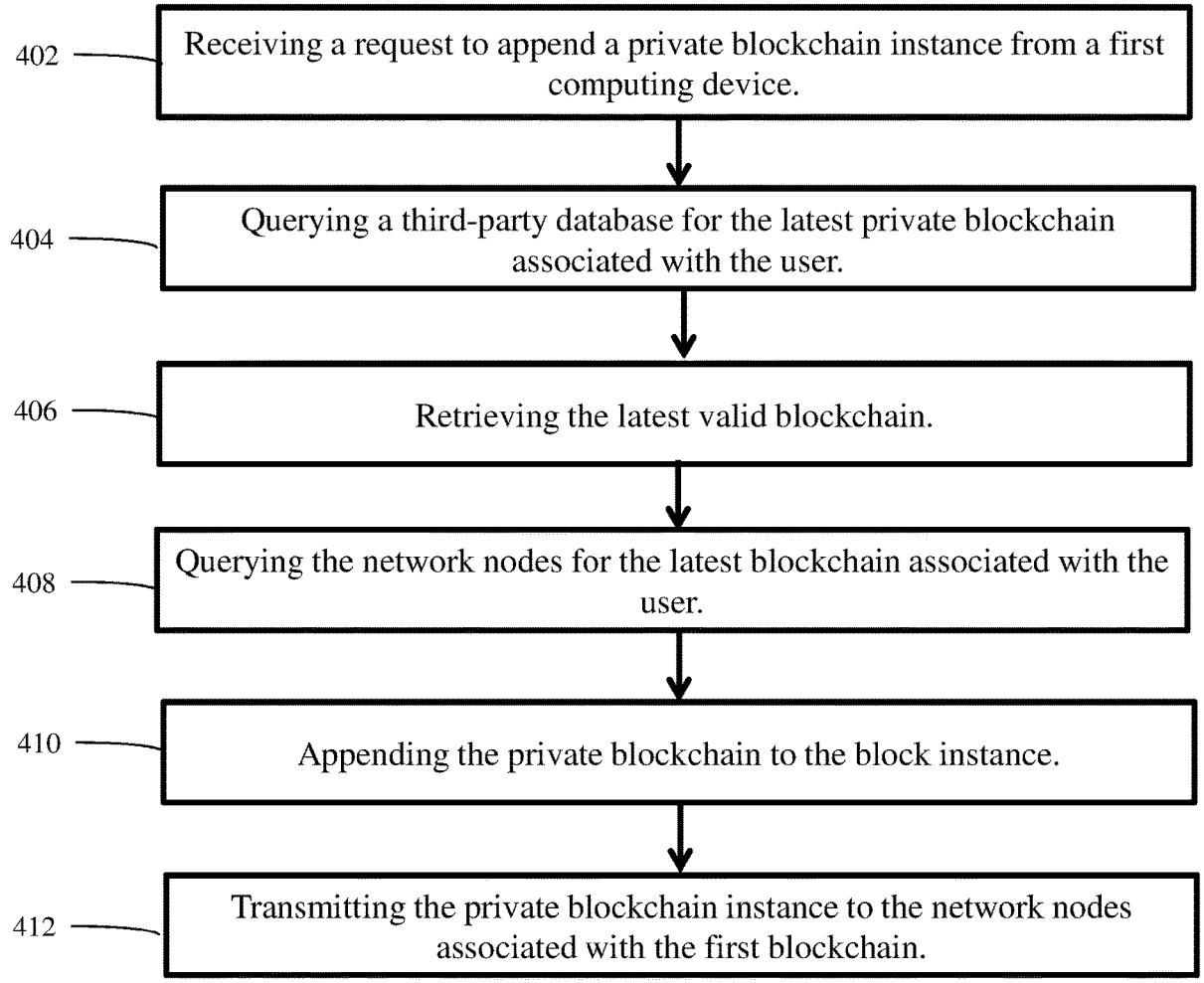
FIG. 4 illustrates a flowchart depicting operational steps for retrieving and appending multiple blockchains, according to an embodiment.

FIG. 4 illustrates execution of an exemplary method 400 for retrieving and appending a private electronic health blockchain to an existing (or new) health blockchain, according to an exemplary embodiment. Other embodiments may comprise additional or alternative steps, or may omit some steps altogether.

At 402, the analytics server may receive a request to append a private blockchain to an existing blockchain. As explained above, the analytics server may generate a graphical user interface in order to provide health record services to variety of clients. In an embodiment, the graphical user interface may be a website hosted by the analytics server, which is available to different clients. The purpose of said website may be to collect health information, provide a platform to securely upload health data, and/or possibly retrieve health data from the website. The graphical user interface may act as an intermediary between different parties involved within a user's career and may be a central and "one stop" place for adding, updating, and/or retrieving data. While the described graphical user interface is described herein as a central management tool, neither the analytics server nor the graphical user interface deviate from the spirit of the distributed nature of the blockchain technology. The analytics server provides a management tool to reduce computational burden of keeping record within different and unrelated databases; blockchain instances may be stored in individual client databases (network nodes).

The analytics server may receive a request from a first computing device to append a private blockchain to an existing health blockchain maintained by the analytics server. A private blockchain is a blockchain, which is maintained and managed by a server (not associated or affiliated with the analytics server), which may only accept new information and block instances from certain designated computing devices. A non-limiting example of a private blockchain may include an internal company blockchain. For example, a company may generate and maintain a blockchain configured to only accept information or generate new block instances from computing devices within that company.

In an embodiment, the analytics server may receive the request from a former employee of a company, which utilizes a private blockchain. In an embodiment, the analytics server may receive a request from a first computing device utilized by the employee. The employee may desire to attach his/her private blockchain to his/her health blockchain managed by the analytics server. The analytics server (as described in FIG. 2 and FIG. 3) may manage employee's health blockchain. Employee's private blockchain may contain information associated with specific work-related data, which may not be made public by the employee's former health service provider.

For example, the private blockchain may contain recommendations, writing samples, trophies and awards, and other pertinent information, which the employee may desire to catalog to his health blockchain. In an embodiment, the employee's health blockchain includes a block instance associated with the former health service provider, however does not include the private blockchain. As a result, not all the network nodes within the blockchain may see all the pertinent information. The analytics server may receive identification associated with the block instance and the network node associated with the block instance. For example, a former employee may identify that he would like to append a private internal blockchain (another health service provider) to his health records.

At 404, the analytics server may query a third party database for the latest valid blockchain associated with the user. The analytics server may identify the network node associated with the private blockchain and query the network node or a database associated with the network node by sending an instruction configured to receive the private blockchain from the network node/database. For example if the private blockchain is associated with network node A, the analytics server may generate and transmit the instruction to network node A. The analytics server may identify the network node associated with the private blockchain by using the identification received in step 402. The analytics server may transmit said instruction to the network node or directly to a database associated with the network node and receive the private blockchain associated with the employee.

At 406, the analytics server may receive the latest valid private blockchain associated with the user. The analytics server may query the network node to request the latest valid private blockchain. In some embodiments, the analytics server may generate and transmit an instruction to the network node to poll all the internal/private network nodes and receive the latest valid private blockchain. In other embodiments, the analytics server may transmit an instruction to the network node to identify the private network nodes, generate, and transmit another instruction directly to the private network nodes in order to receive the latest valid private blockchain. Private network nodes, as used herein, are internal nodes within the private blockchain system, which possess each private block instance.

For example, a private blockchain belonging to company A may comprise three private block instances associated with accounting, pharmacy, and physicians. In this example, each of accounting, pharmacy, and physicians may represent a private network node (e.g., are associated with block instances that are private). The analytics server may contact each of the above-mentioned three private network nodes and query for the latest valid private health blockchain.

At 408, the analytics server may query for the latest valid health blockchain associated with the user. As explained above, the analytics server may poll the network nodes associated with the health blockchain instances within the user's health blockchain and determine the latest valid blockchain. The analytics server may use a predetermined threshold for determining the latest valid blockchain. For example, the analytics server may query the network nodes for the latest blockchain instance.

If the analytics server receives the same blockchain from 51% of the network nodes, the analytics server may determine that the received blockchain is the latest valid blockchain. The predetermined threshold is set upon the level of integrity required for the data and instructions stored in the analytics server or the blockchain. In some embodiments, the analytics server may receive the level of integrity (e.g., the threshold to determine the latest valid blockchain) from the user, the first computing device, or the second computing device. The analytics server may use a higher predetermined threshold for data requiring a higher level of security and integrity, for example, electronic money transfers. While the present embodiment only describes two computing device for the simplicity purposes, the user's health blockchain may include several computer nodes.

At 410 and 412, the analytics server may append the private blockchain to the health blockchain by transmitting the private blockchain to the network nodes associated with the health blockchain. As explained above, the analytics server may generate a hash value for the private blockchain based on the hash value of the identified block instance and append the private blockchain to the specific block instance associated with the network node associated with the private blockchain and the block instance (See FIG. 4).

The analytics server may also replicate the private blockchain or generate a link to the private blockchain (depending on the network node associated with the private blockchain). The analytics server may also transmit the private blockchain (block instances within the private blockchain) to all the network nodes associated with the health blockchain.

Figure 5:
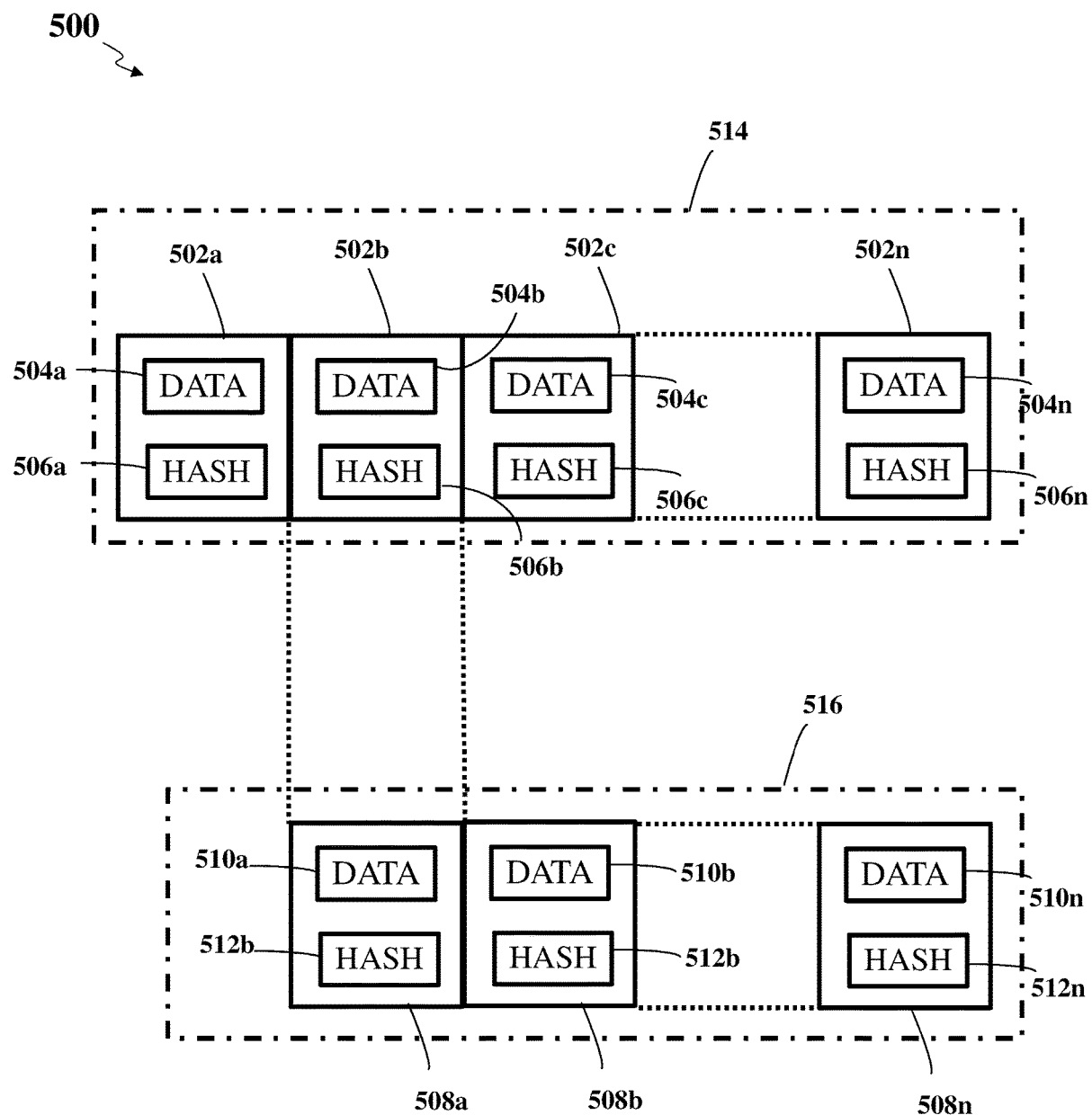
FIG. 5 graphically illustrates an example of appending a private blockchain to an intelligent health blockchain, according to an embodiment.

Referring now to FIG. 5, an example of appending a private blockchain to a user's health blockchain is illustrated. As depicted in FIG. 5, an health blockchain 514 comprises block instances 502a-502n (collectively 502) that include data 504a-504n (collectively 504) that enables information, such as health data, machine-readable code/documents, and other metadata associated with a user is illustrated. Also contained in the blockchain instances are hash values 506a-506n (collectively 506) that are used to link each of the block instances to the preceding blockchain instances or blockchain formed by the preceding blockchain instances, as understood in the art.

As explained above, private blockchain 516 may be associated with a network node within the health blockchain 514. The health blockchain 514 may comprises block instances (e.g., block instances 502a-n) relating to health of a user. Private blockchain 516 may belong to the network node associated with the block instance 502b. For example, network node associated with the block instance 502b may be a former health service provider (e.g., company A), which provides a limited, internal, and private blockchain within company A. As depicted within this embodiment, the analytics server may receive a request to append private blockchain 516 to the health blockchain 514. The user may receive this request after the user has left company A and now desires to update his resume using data included within the private blockchain 516.

As depicted in FIG. 5, the private blockchain 516 comprises block instances 508a-508n (collectively 508) that include data 510a-510n (collectively 510) that enables information, such as health data, machine-readable code/documents, and other metadata associated with a user is illustrated. Also contained in the blockchain instances are hash values 512a-512n (collectively 512) that are used to link each of the private block instances to the preceding blockchain instances. Each block instance within the private blockchain 516 (e.g., private block instances) may be associated with different private network nodes within the blockchain system provided by the network node associated with blockchain 502b. For example private block instance 508a may belong to (e.g., be stored locally at a database associated with) private network node A and private block instance 508b may belong to private network node B.

Upon receiving a request from the user's computing device, the analytics server may generate and transmit an instruction configured to receive the private blockchain 516 from the network node associated with block instance 502b. Upon transmission of the instruction, the analytics server may receive the private blockchain 516. In some other embodiments, the analytics server may query and identified the associated network nodes and query them directly to retrieve the blockchain. The analytics server may append the private blockchain 516 to the block instance 502b and generate a parallel or ancillary blockchain. As depicted in FIG. 5, private blockchain 516 is parallel to health blockchain 514. In some embodiments, the analytics server may only append the private blockchain 516 to the block instance 502b. The analytics server may also transmit a notification to the network nodes associated with each block instance within the health blockchain that a new parallel blockchain has been generated and append to the original blockchain. In some embodiments, the analytics server may transmit the content of the private blockchain to all the networks nodes within the health blockchain 514. The analytics server may also first identify the public and private information within the private blockchain 516 and transmit/share the data within the private blockchain 516 with in accordance to this designation.

Figure 6:
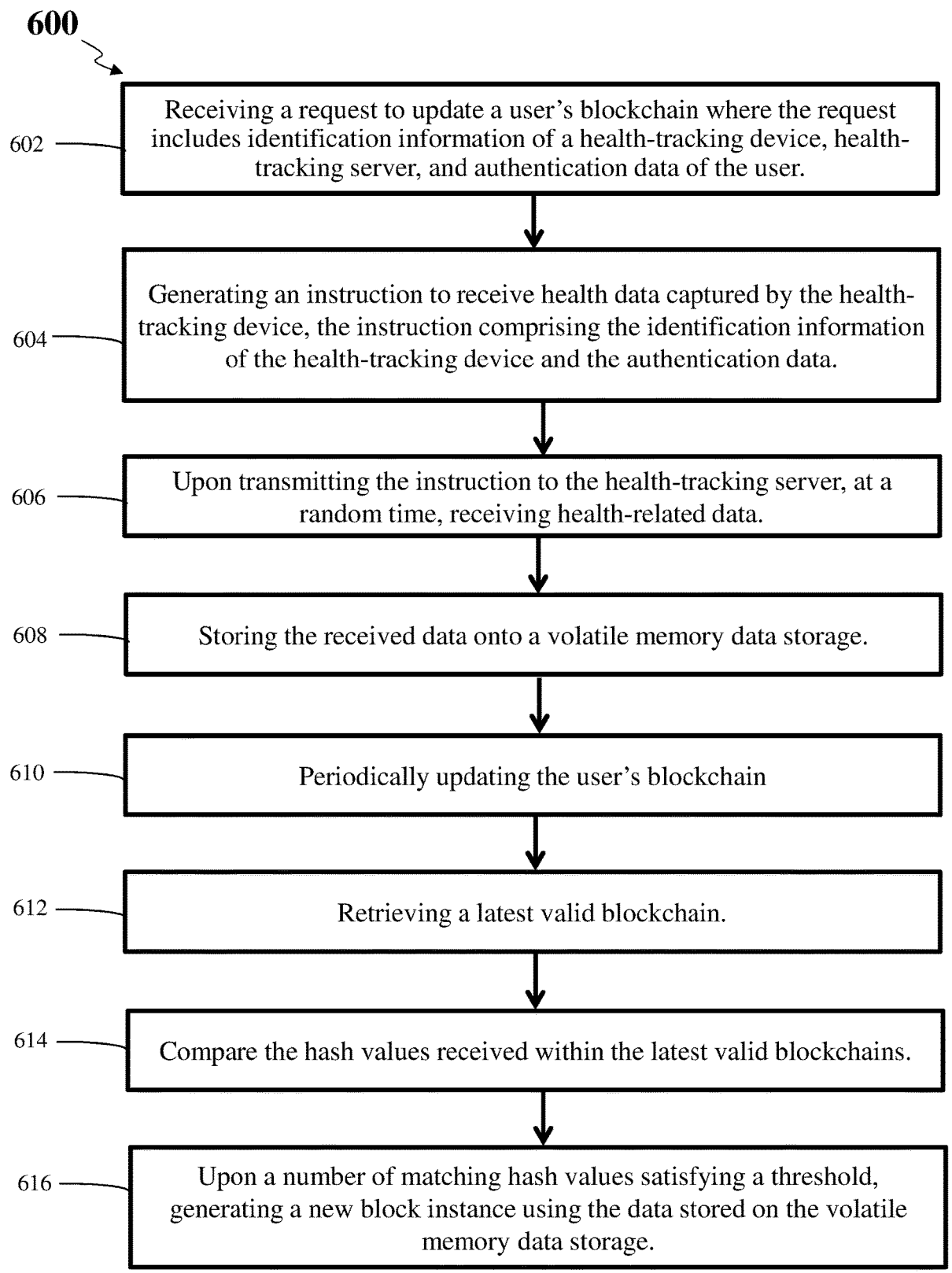
FIG. 6 illustrates a flowchart depicting operational steps for generating an intelligent health-based blockchain, according to an embodiment.

FIG. 6 illustrated execution of an exemplary method 600 for generating an intelligent health blockchain, according to an exemplary embodiment. Other embodiments may comprise additional or alternative steps, or may omit some steps altogether.

At step 602, the analytics server may receive a request to update a health blockchain including identification information of the health-tracking device, health-tracking server, and authentication data. The analytics server may receive, from an electronic device operated by a user, a request to update a blockchain of the user, the request comprising identification information associated with a health-tracking sensor, a second server associated with the health-tracking sensor, and user authentication data. The analytics server may receive this request via the graphical user interface provided by the analytics server to different network nodes. For example, a user may desire to add third-party health data (e.g., exercise information from a wearable device, or other health-tracking devices) to his health blockchain.

In some configurations, the user may log into the website provided by the analytics server (the graphical user interface as described above) and log into his account using the blockchain key (or any other authentication method) provided by the analytics server (described above). The user may also provide identification information regarding the health-tracking device. For example, the user may input the serial number identifying the health-tracking device or a login credentials associated with the health-tracking device (login and password associated with the server associated with the health-tracking device or other credentials granting access to a server of the health-tracking device to retrieve user's health data).

In some embodiments, the user may transmit a pre-generated token (by the fitness server or a third party) to the analytics server, which may act as continuous authentication and grant the analytics server access to a server associated with the fitness tracker.

In some configurations, the website operated by the analytics server may comprise one or more inputs fields configured to receive authentication data e.g., login credentials associated with the fitness tracker). For instance, the user may input his authentication data. In some embodiments, the website operated by the analytics server may look similar to the corresponding interface from the health-tracking device. In other words, the analytics server may preserve the "look and feel" of the login webpage of the users identified health-tracking device. To achieve this, the analytics server may identify the login webpage for the user's health-tracking device and update a browser plate within the webpage displayed on the user's client device with at least a portion of the login webpage for the user's health-tracking device.

At step 604, the analytics server may generate an instruction to receive health data captured by the health-tracking sensor, the instruction comprising the identification information associated with the health-tracking sensor and the user authentication data. The analytics server may identify a server associated with the request received (step 602) and generate an instruction to receive (e.g., query) health-related data associated with the user. The analytics server may be authorized using authorization credentials received within the request (step 602). For example, using the login and passcode provided by the user, the analytics server may authenticate itself and have full access to the server associated with the fitness tracker/wearable. The analytics server may then request (e.g., query) data from the server. The analytics server may generate an instruction to receive all health-related data (e.g., number of steps, heartbeat pattern, sleep duration and intensity, physical exercise intensity and duration, and the like) form the server associated with the health-tracking device. At step 606, the analytics server may transmit the instruction (generated in step 604) to the health-tracking server, at a random time, and upon this transmission, the analytics server may receive health-related data from the fitness tracker server. As discussed below, the transmission of the instruction may be at random times to decrease the chance of fraudulent activity.

In order to minimize/reduce the chance of data compromise, the analytics server may query and retrieve health-related data at random times. For instance, the analytics server may query a user's health-tracking device at 1 AM, 2 PM, 8 PM, and 9:30 PM. The analytics server may store the data received, as a result of each query, in the volatile memory data storage. Subsequently, as described above, the analytics server may aggregate the data received, as a result of each query, and generate a single block instance that corresponds to a predetermined interval (e.g., 24 hours).

At step 608, the analytics server may transmit and store the received data onto a volatile memory data storage. As described above, in order to reduce the computing and processing power needed to generate a blockchain, the analytics server may temporarily store the data received from the users' health-tracking devices (via their respective servers) onto a volatile memory data storage. This process allows the analytics server to generate fewer block instances, which results in less computing power needed and/or consumed. Furthermore, the blockchain created by the analytics server may comprise block instances that correspond to consistent time intervals. For instance, data transmittal from the users' health-tracking devices and/or health-tracking servers may not be transmitted consistently (e.g., with consistent frequency of data transmittal). This may be due to technical errors (e.g., data interruptions, bad connections, and the like) that cannot be directly remedied by the analytics server. In order to overcome this technical hurdle, the analytics server may store the data received in the volatile memory data storage, manipulate the data by normalizing and/or unifying different data types, and generating block instance that only correspond to a predetermined time. In this way, less computing power is consumed when generating and maintaining the blockchain because fewer block instances are generated. Furthermore, when analyzing the data stored onto the blockchain, less computing power is needed because fewer block instances are analyzed.

In a non-limiting example, the analytics server may receive data corresponding to a user's physical activity every three hours. The analytics server may receive multiple health-related data from multiple and disparate data sources for the same user. For instance, the analytics server may also receive a second set of health-related data for the same user from a different health-tracking device every five hours. Generating a block instance for the user's activity will inevitably require a high processing power because the analytics server will have to validate the blockchain every three hours, generate a new block instance every three hours, and append the newly generated block instance every three hours. Furthermore, the analytics server may have to repeat the above-mentioned process every five hours for the second set of health-related data.

In order to reduce the above-described computing power, the analytics server may store the user's health data (received every three hours from the first health-tracking device and every five hours from the second health-tracking device) in the volatile memory. Subsequently, based on a predetermined time interval (e.g., every day, every two days, or any other frequency) the analytics server may retrieve all data associated with the user, aggregate all data collected, and generate a single block instance that corresponds to the user's data. For instance, instead of generating eight block instances for the first health-tracking device and five block instances for the health-tracking device in one day, the analytics server may generate a single block instance that includes the above-mentioned data collectively. Utilizing the method described above, the analytics server can significantly reduce the processing power and the time needed to generate and operate the user's health blockchain. The analytics server can also significantly reduce the computing power needed to analyze the user's health-related data.

At step 610, the analytics server may periodically update the blockchain of the user based on the health data stored in the volatile memory storage. As discussed below, the analytic server may periodically update the user's blockchain in accordance with data stored in the volatile memory data storage. For instance, every 12 or 24 hours, the analytic server may aggregate all data from various devices associated with the user and store the collected and aggregated data in a block instance. The analytics server may also update the user's blockchain accordingly. In this way, the analytic server generates a block instance that comprises all health-related data of the user for the determined period of time. The analytic server may update the blockchain using the methods and embodiments described herein. For example, the analytic server may perform steps 612-616 to update the user's blockchain.

The analytics server may (upon receiving proper authorization from the user) continuously and/or periodically update the health blockchain with the health-related data. For example, the analytics server may update the health blockchain every day, once a week, at another pre-determined period, or based on a time interval received form the user. In another embodiment, the analytics server may receive a notification from the fitness tracker server and update the health blockchain indicating that the user has generated new data (e.g., the fitness tracker server has detected a new physical activity session). The analytics server may then query for new data and update the health blockchain accordingly.

In some configurations, the health-related data, received by the analytics server, may be in different formats. For instance, the analytics server may update the user's blockchain with data received from multiple-health-tracking devices or disparate data sources. The analytics server may normalize (e.g., create a uniform type of data) the received data into standard format and aggregate the data into a single file before storing the file onto the volatile memory data storage. In some embodiments, the analytics server may create a single JavaScript Object Notation (JSON) format file for each user and may generate the block instance in accordance with JSON file.

The JSON file may include data received from different health-tracking devices having different file types or formats. For example, the data generated by a user's Fitbit® may include sleep pattern, but may not include user's heart rate. Furthermore, data generated by user's Apple® Watch may include user's heart rate data and the sleeping pattern. Furthermore, the data files received from the server associated with the user's Fitbit® may utilize a different format from the user's Apple® Watch. The analytics server may initially collect all data from both devices with different file formats, aggregate the data from different devices into a single JSON file for each user. As a result, the JSON file may include sleep pattern information from the Fitbit® device and heart rate information from Apple® Watch. The JSON file may be then be stored onto the volatile memory data storage. In some configurations, the analytics server my only generate a single block instance for every user's JSON file.

FIG. 7 illustrates an example of aggregating data from different devices into a uniform JSON file, according to an embodiment. In the depicted embodiment, the analytics server receives data from wearable device 1, wearable device 2, IoT device 1, and IoT device 2. As illustrated, different devices may comprise different health attributes captured by each health-tracking device. For instance, rows 702-8 illustrate that some health-tracking devices do not capture similar health attributes associated with the user. For example, wearable device 1 may not be configured to collect data associated with the user's sleep pattern; Wearable device 2 may be configured to collect data associated with the user's heart rate; IoT device 1 may be configured to collect data associated with the user's sleep pattern (e.g., smart mattress); IoT device 2 may be configured to collect data associated with the user's driving habits (e.g., IoT device installed and the user's vehicle). Furthermore, some health-tracking devices may capture inconsistent data. For instance, wearable device 2 and wearable device 2 have captured different heart rates for the user.

As illustrated, the analytics server may receive data from disparate data sources and may aggregate such data into a JSON file 710. The aggregated data 710 may include data associated with each attribute. The aggregating process may also calculate an average value for data associated with the same attribute, as illustrated regarding the user's heart rate. In some configurations, the analytics server may generate the JSON file 710 periodically (e.g., once a day). The analytics server may store the JSON file 710 on to the volatile memory data storage and may generate a block instance for JSON 710.

As described above, the analytics server may periodically retrieve data from one or more health-tracking devices. However, in some configurations, the analytics server may modify this frequency of data capture. For instance, the analytics server may capture user's heart rate from a wearable device operated by a user every 12 hours. However, if the analytics server identifies inconsistent data, the analytics server may increase the above-mentioned frequency (e.g., every 3 hours). In a non-limiting example, the analytics server receives data from a user's wearable heart rate monitor and a number of steps taken by the user from another health-tracking device associated with the user (e.g., pedometer from the user's mobile device). If the analytics server receives inconsistent data (e.g., the user's heart rate is not elevated while the second health-tracking device indicates that the user is exercising) the analytics server may generate an instruction for an immediate and/or a more frequent transmittal of health-related data. The analytics server may also transmit that instruction to the user's wearable heart rate monitor and/or mobile device.

Referring back to FIG. 6, at step 612, the analytics server may retrieve a plurality of latest valid block instances associated with the user from a plurality of network nodes, each block instance comprising encrypted health data associated with the user and a corresponding hash value, wherein each block instance is stored in a database associated with at least one of the plurality of network nodes. As described above, the analytic server may transmit an instruction to all or some (depending on a predetermined quorum threshold) of the network nodes where the instruction causes the network node to transmit a latest valid blockchain. As described above, each network node may possess a copy of the latest valid blockchain comprising multiple block instances and their corresponding hash values. In some implementations, to deploy the second block instance to the user's health blockchain, the analytics server may poll the network nodes associated with the blockchain instances within the user's health blockchain and determine the latest valid blockchain. The analytics server may use a predetermined threshold for determining the latest valid blockchain. For example, the analytics server may query the network nodes (different fitness tracker servers) for the latest blockchain instance.

At step 614, the analytics server may compare the hash value associated with each block instance within the plurality of latest valid block instances with each respective hash value associated with each respective block instance within each latest valid blockchain received from each network node of the plurality of network nodes. Simply put, the analytic server may compare the hash value of each block instance with the hash value of the corresponding block instances within each received latest valid blockchain from each network node.

As described above, if the analytics server receives the same blockchain from 51% of the network nodes, the analytics server may determine that the received blockchain is the latest valid blockchain. In some embodiments, the analytics server may generate and transmit an instruction to all the network nodes associated with other block instances within the health blockchain and notify the parties that a validation process has been initiated and that the network node's participation is requested.

The predetermined threshold is set upon the level of integrity required for the data and instructions stored in the analytics server or the blockchain. In some embodiments, the analytics server may receive the level of integrity (e.g., the threshold to determine the latest valid blockchain) from the client device (e.g., the user), the first computing device, the second computing device, or any other network node or computing device associated with the blockchain. The analytics server may use a higher predetermined threshold for data requiring a higher level of security and integrity, for example, recognition point transfers or sensitive recommendation/data transfer. While the present embodiment only describes two computing device for the simplicity purposes, the user's health blockchain may include several computer nodes and the analytics server may poll all the nodes associated with a blockchain to receive the latest valid blockchain. In an embodiment, the analytics server may contact every node associated with the blockchain and request to receive each node's latest valid blockchain. Upon receipt of the latest valid blockchain of each network node (including the hash values for each block instance), the analytics server may match the received hash values from each node with each other. Upon the number of positive matches satisfying a threshold, the analytics server assumes that the received blockchain is the latest valid blockchain.

At step 616, upon a number of matching hash values satisfying a pre-determined threshold, the analytics server may generate a new block instance comprising the health data stored within the volatile memory storage and a new hash value based at least on one of the user, the health data captured by the health-tracking sensor, the second server, and the user computing device, according to a hashing algorithm. The analytic server may append the newly generated block instance to the latest valid blockchain. As described above, the analytic server may append the newly generated block instance to the user blockchain.

The analytics server may generate a hash value using the user's identification (e.g., user's identification or other identifying values associated with the user), health-data received (step 606), and/or the network node (e.g., the computing device used by the user). The hash value may be non-interactive and/or may have no secret/encryption keys that have to be managed by a central server or relying party (e.g., the analytics server or another central server). The hash value may be a cryptographic hash function. For example, in some embodiments, the hash value may be a string of alphanumerical values. The analytics server may generate the hash value based on the received data from the computing device. For example, data inputted in the one or more data fields of the graphical user interface may be hashed according to a predetermined hashing algorithm, combined together, and then stored to the blockchain instance. As explained above, the analytics server may hash portions of the first block separately to create intermediate hash values and generate a final hash value based on the intermediate hash values and store the final hash value in the first blockchain instance.

Alternatively, the analytics server may hash the entire content of the first block instance to generate the final hash value and store the hash value in the first blockchain instance. The analytics server may append a new block instance to a block instance (of the latest valid blockchain). The analytics server may, as described above, transmit a copy of the latest block instance to all the other network nodes associated with the health blockchain. Furthermore, in some configurations, the analytics server may purge the content of the volatile memory data storage after updating the blockchain.

The foregoing method descriptions and the process flow diagrams are provided merely as illustrative examples and are not intended to require or imply that the steps of the various embodiments must be performed in the order presented. The steps in the foregoing embodiments may be performed in any order. Words such as "then," "next," etc. are not intended to limit the order of the steps; these words are simply used to guide the reader through the description of the methods. Although process flow diagrams may describe the operations as a sequential process, many of the operations can be performed in parallel or concurrently. In addition, the order of the operations may be re-arranged. A process may correspond to a method, a function, a procedure, a subroutine, a subprogram, and the like. When a process corresponds to a function, the process termination may correspond to a return of the function to a calling function or a main function.

The various illustrative logical blocks, modules, circuits, and algorithm steps described in connection with the embodiments disclosed herein may be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the present embodiments.

Embodiments implemented in computer software may be implemented in software, firmware, middleware, microcode, hardware description languages, or any combination thereof. A code segment or machine-executable instructions may represent a procedure, a function, a subprogram, a program, a routine, a subroutine, a module, a software package, a class, or any combination of instructions, data structures, or program statements. A code segment may be coupled to another code segment or a hardware circuit by passing and/or receiving information, data, arguments, parameters, or memory contents. Information, arguments, parameters, data, etc. may be passed, forwarded, or transmitted via any suitable means including memory sharing, message passing, token passing, network transmission, etc.

The actual software code or specialized control hardware used to implement these systems and methods is not limiting of the present disclosure. Thus, the operation and behavior of the systems and methods were described without reference to the specific software code being understood that software and control hardware can be designed to implement the systems and methods based on the description herein.

When implemented in software, the functions may be stored as one or more instructions or code on a non-transitory computer-readable or processor-readable storage medium. The steps of a method or algorithm disclosed herein may be embodied in a processor-executable software module, which may reside on a computer-readable or processor-readable storage medium. A non-transitory computer-readable or processor-readable media includes both computer storage media and tangible storage media that facilitate transfer of a computer program from one place to another. A non-transitory processor-readable storage media may be any available media that may be accessed by a computer. By way of example, and not limitation, such non-transitory processor-readable media may comprise RAM, ROM, EEPROM, CD-ROM or other optical disk storage, magnetic disk storage or other magnetic storage devices, or any other tangible storage medium that may be used to store desired program code in the form of instructions or data structures and that may be accessed by a computer or processor. Disk and disc, as used herein, include compact disc (CD), laser disc, optical disc, digital versatile disc (DVD), floppy disk, and Blu-ray disc where disks usually reproduce data magnetically, while discs reproduce data optically with lasers. Combinations of the above should also be included within the scope of computer-readable media. Additionally, the operations of a method or algorithm may reside as one or any combination or set of codes and/or instructions on a non-transitory processor-readable medium and/or computer-readable medium, which may be incorporated into a computer program product.

The preceding description of the disclosed embodiments is provided to enable any person skilled in the art to make or use the present disclosure. Various modifications to these embodiments will be readily apparent to those skilled in the art, and the generic principles defined herein may be applied to other embodiments without departing from the spirit or scope of the disclosed embodiments. Thus, the present disclosure is not intended to be limited to the embodiments shown herein but is to be accorded the widest scope consistent with the following claims and the principles and novel features disclosed herein.

While various aspects and embodiments have been disclosed, other aspects and embodiments are contemplated. The various aspects and embodiments disclosed are for purposes of illustration and are not intended to be limiting, with the true scope and spirit being indicated by the following claims.

What is claimed is:

1. A computer-implemented method comprising:
   receiving, by a first server from an electronic device operated by a user, a request to update a blockchain of the user, the request comprising identification information associated with a health-tracking sensor, an identification of a second server associated with the health-tracking sensor, and user authentication data;
   generating, by the first server, an instruction to receive health data captured by the health-tracking sensor, the instruction comprising the identification information associated with the health-tracking sensor and the user authentication data;
   upon transmitting the instruction to the second server, at a random time, receiving, by the first server, the health data captured by the health-tracking sensor;
   storing, by the first server, the health data captured by the health-tracking sensor in a volatile memory storage;
   periodically updating, by the first server, the blockchain of the user based on the health data captured by the health-tracking sensor and stored in the volatile memory storage where updating comprises:
      retrieving, by the first server, a plurality of latest valid block instances associated with the user from a plurality of network nodes, each block instance comprising encrypted data associated with the user and a corresponding hash value, wherein each block instance is stored in a database associated with at least one of the plurality of network nodes;
      comparing, by the first server, the hash value associated with each block instance within the plurality of latest valid block instances with each respective hash value associated with each respective block instance within each latest valid blockchain received from each network node of the plurality of network nodes; and
      upon a number of matching hash values satisfying a pre-determined threshold, generating, by the first server, a new block instance comprising the health data captured by the health-tracking sensor and stored within the volatile memory storage and a new hash value corresponding to at least one of the user, the health data captured by the health-tracking sensor, the identification of the second server, or the user computing device.

2. The method of claim 1, wherein the first server updates the blockchain using data stored on to the volatile memory storage in accordance with a predetermined frequency.

3. The method of claim 2, wherein the predetermined frequency is received from the electronic device operated by the user.

4. The method of claim 1, wherein the user authentication data comprises login information associated with the second server and the user.

5. The method of claim 1, wherein the health-tracking sensor is a wearable device.

6. The method of claim 1, wherein the user authentication data comprises an authentication token.

7. The method of claim 6, wherein the authentication token is received, by the first server, from the electronic device.

8. The method of claim 6, wherein the authentication token is received, by the first server, from the second server.

9. The method of claim 1, wherein the first server instructs the health-tracking sensor to transmit the health data captured in accordance with a predetermined frequency.

10. The method of claim 9, wherein the first server modifies the predetermined frequency in accordance with one or more criteria.

11. A computer system comprising:
   an electronic device operated by a user;
   a health-tracking sensor configured to captured health data associated with the user, the health-tracking device further configured to transmit the captured health data to a first server;
   a plurality of network nodes where each network node is configured to store at least one block instance of a blockchain of a user;
   a second server in communication with the health-tracking sensor, the first server, the plurality of network nodes, and the electronic device, the second server configured to:
      receive, from the electronic device, a request to update the blockchain of the user, the request comprising identification information associated with the health-tracking sensor, an identification of a second server associated with the health-tracking sensor, and user authentication data;

generate a first instruction to receive health data captured by the health-tracking sensor, the first instruction comprising the identification information associated with the health-tracking sensor and the user authentication data;

upon transmitting the first instruction to the first server, receive health data captured by the health-tracking sensor;

store the health data captured by the health-tracking sensor in a volatile memory storage;

periodically update the blockchain of the user based on the health data stored in the volatile memory storage where updating comprises:

retrieve a plurality of latest valid block instances associated with the user from the plurality of network nodes, each block instance comprising encrypted data associated with the user and a corresponding hash value, wherein each block instance is stored in a database associated with at least one of the plurality of network nodes;

compare the hash value associated with each block instance within the plurality of latest valid block instances with each respective hash value associated with each respective block instance within each latest valid blockchain received from each network node of the plurality of network nodes;

upon a number of matching hash values satisfying a pre-determined threshold:

generate a new block instance comprising the health data captured by the health-tracking sensor and stored within the volatile memory storage and a new hash value based corresponding to at least one of the user, the health data captured by the health-tracking sensor, the identification of the second server, or the user computing device.

12. The computer system of claim 11, wherein the first server updates the blockchain using data stored on to the volatile memory storage in accordance with a predetermined frequency.

13. The computer system of claim 12, wherein the predetermined frequency is received from the electronic device operated by the user.

14. The computer system of claim 11, wherein the user authentication data comprises login information associated with the second server and the user.

15. The computer system of claim 11, wherein the health-tracking sensor is a wearable device.

16. The computer system of claim 11, wherein the user authentication data comprises an authentication token.

17. The computer system of claim 16, wherein the authentication token is received, by the first server, from the electronic device.

18. The computer system of claim 16, wherein the authentication token is received, by the first server, from the second server.

19. The computer system of claim 11, wherein the first server instructs the health-tracking sensor to transmit the health data captured in accordance with a predetermined frequency.

20. The computer system of claim 19, wherein the first server modifies the predetermined frequency in accordance with one or more criteria.

* * * * *